(12) United States Patent
Hayashi et al.

(10) Patent No.: US 7,345,170 B2
(45) Date of Patent: Mar. 18, 2008

(54) CRYSTAL AND SOLVATE OF 2-AMINO-6-BENZYLOXYPURINE AND PRODUCTION METHODS THEREOF

(75) Inventors: Taketo Hayashi, Osaka (JP); Takehiko Kawakami, Osaka (JP); Yoshihiko Iwanaga, Osaka (JP); Yosuke Watanabe, Osaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 504 days.

(21) Appl. No.: 10/500,451

(22) PCT Filed: Apr. 3, 2003

(86) PCT No.: PCT/JP03/04258

§ 371 (c)(1),
(2), (4) Date: Sep. 16, 2004

(87) PCT Pub. No.: WO03/084957

PCT Pub. Date: Oct. 16, 2003

(65) Prior Publication Data

US 2005/0080098 A1 Apr. 14, 2005

(30) Foreign Application Priority Data

Apr. 8, 2002 (JP) .............................. 2002-105805

(51) Int. Cl.
*C07D 473/18* (2006.01)
(52) U.S. Cl. .................................................. 544/276
(58) Field of Classification Search .................... None
See application file for complete search history.

(56) References Cited

U.S. PATENT DOCUMENTS

| 4,801,710 A * | 1/1989 | MacCoss et al. ........... 544/244 |
| 5,352,669 A * | 10/1994 | Moschel et al. .............. 514/45 |
| 6,184,376 B1 * | 2/2001 | Leanna et al. .............. 544/229 |
| 6,414,112 B1 * | 7/2002 | Buchardt et al. ........... 530/300 |

FOREIGN PATENT DOCUMENTS

| JP | 06116266 A * | 4/1994 |
| JP | 10-218880 A | 8/1998 |
| WO | WO 00/08025 A1 | 2/2000 |

OTHER PUBLICATIONS

Seela, Science of Synthesis (2004), 16, p. 1058.*
Spassova, et al., Collection of Czechoslovak Chemical Communications (1994), 59(5), 1153-74.*
MacCross, Tetrahedron Letters (1985), 26(15), 1815-18.*
Bzowska, Z. Naturforsch. 54c, 1055-1067 (1999).*
Translation of JP 06116266 A.*
Bowles et al., *Journal of Medicinal Chemistry*, 6, pp. 471-480 (1963).
Robins et al., *Journal of Organic Chemistry*, 34(7), pp. 2160-2163 (1969).

* cited by examiner

*Primary Examiner*—Mark L. Berch
(74) *Attorney, Agent, or Firm*—Leydig, Voit & Mayer, Ltd.

(57) ABSTRACT

The present invention can provide a solvate, a cubic crystal and a columnar crystal of 2-amino-6-benzyloxypurine by crystallization from (1) a solvent containing at least one kind of solvent selected from the group consisting of alcohol and water, (2) alcohol or (3) a water-containing solvent.

3 Claims, 18 Drawing Sheets

CRYSTAL AND SOLVATE OF 2-AMINO-6-BENZYLOXYPURINE AND PRODUCTION METHODS THEREOF

TECHNICAL FIELD

The present invention relates to a novel crystal and a solvate of 2-amino-6-benzyloxypurine and production methods thereof.

BACKGROUND ART

2-Amino-6-benzyloxypurine is useful as an intermediate for the production of a pharmaceutical product, and there are various reports on the production methods thereof. However, no report relates to the production of 2-amino-6-benzyloxypurine as a solvate (e.g., hydrate, methanolate), and there is no report relating to the production method of the solvate.

As regards a crystal of 2-amino-6-benzyloxypurine, for example, The Journal of Organic Chemistry, vol. 34, 2160-2163 (1969) reports that a needle crystal can be obtained. However, the number of reports is small, with no report on a cubic crystal or a columnar crystal obtained so far or production methods thereof.

It is therefore an object of the present invention is to provide a method for producing 2-amino-6-benzyloxypurine as a crystal having a shape so far not obtained, namely, as a cubic crystal or a columnar crystal. Another object of the present invention is to provide a method for producing a 2-amino-6-benzyloxypurine solvate (particularly hydrate or alcoholate). A further object of the present invention is to provide a cubic crystal, a columnar crystal and a solvate (particularly hydrate or alcoholate) of 2-amino-6-benzyloxypurine.

DISCLOSURE OF THE INVENTION

The present inventors have intensively studied in an attempt to achieve the above-mentioned objects, and found a solvate (particularly hydrate and alcoholate), a cubic crystal and a columnar crystal of 2-amino-6-benzyloxypurine heretofore not obtained and production methods thereof, which resulted in the completion of the present invention.

That is, the present invention provides the following [1]-[12].

[1] A 2-amino-6-benzyloxypurine solvate.
[2] A 2-amino-6-benzyloxypurine hydrate.
[3] A 2-amino-6-benzyloxypurine alcoholate.
[4] A 2-amino-6-benzyloxypurine methanolate.
[5] A 2-amino-6-benzyloxypurine ethanolate.
[6] A cubic crystal of 2-amino-6-benzyloxypurine.
[7] A columnar crystal of 2-amino-6-benzyloxypurine.
[8] A production method of a cubic crystal or a columnar crystal of 2-amino-6-benzyloxypurine, which comprises crystallization from a solvent containing at least one kind of solvent selected from the group consisting of alcohol and water.
[9] A production method of a 2-amino-6-benzyloxypurine alcoholate, which comprises crystallization from alcohol.
[10] A production method of a 2-amino-6-benzyloxypurine hydrate, which comprises crystallization from a water-containing solvent.
[11] The production method of the above-mentioned [10], wherein the water-containing solvent is a mixed solvent of alcohol and water.
[12] The production method of the above-mentioned [10], wherein the water-containing solvent is water.

DETAILED DESCRIPTION OF THE INVENTION

Figure 1:
FIG. 1 shows a microscopic photograph (magnification× 100, 1 graduation=0.02 mm) of a 2-amino-6-benzyloxypurine hydrate, which is a columnar crystal obtained in Example 1.

According to the present invention, a novel crystal and a novel solvate of 2-amino-6-benzyloxypurine, which have not been obtained before, can be produced. The novel crystal that can be produced in the present invention includes a cubic crystal and a columnar crystal, and a solvate that can be produced in the present invention is a hydrate or an alcoholate (e.g., methanolate, ethanolate and the like). These crystals provided by the present invention are superior in filtration performance and improved in operability as compared to conventional ones.

The production methods of a cubic crystal and a columnar crystal of 2-amino-6-benzyloxypurine are explained in the following. It is essential to obtain a cubic crystal and a columnar crystal by crystallization from a solvent containing at least one kind of solvent selected from the group consisting of alcohol and water, and the shape of the crystal can be determined by the temperature at the time of start of the precipitation of crystals (hereinafter to be referred to as an initiation temperature (Ti)). To be specific, 2-amino-6-benzyloxypurine is dissolved in a solvent containing at least one kind of solvent selected from the group consisting of alcohol and water, and crystals are allowed to precipitate by appropriately setting the initiation temperature (Ti). Ti varies depending on the solvent to be used, and when, for example, methanol (alone) is used as a solvent, Ti is adjusted to around 65° C. (60° C.-65° C.) to give a cubic crystal, and adjusted to 30° C.-55° C., preferably 40° C.-45° C., to give a columnar crystal.

For the production of a cubic crystal and a columnar crystal, 2-amino-6-benzyloxypurine is dissolved in a solvent containing at least one kind of solvent selected from the group consisting of alcohol and water.

As the alcohol in the solvent containing at least one kind of solvent selected from the group consisting of alcohol and water, which is used for the production of a cubic crystal and a columnar crystal, alcohol having 1 to 5 carbon atoms (e.g., methanol (MeOH), ethanol, propanol, isopropanol, butanol, pentyl alcohol and the like) can be used, with preference given to methanol and ethanol.

The total amount of the solvent to be used for producing a cubic crystal and a columnar crystal is not subject to any particular limitation as long as 2-amino-6-benzyloxypurine can be dissolved, and varies depending on temperature of heating and the kind of solvent. When methanol (alone) is used as a solvent, for example, the amount is generally 10 ml-1000 ml, preferably 10 ml-300 ml, relative to 1 g of 2-amino-6-benzyloxypurine in the following temperature range.

The heating temperature for dissolving 2-amino-6-benzyloxypurine in a solvent containing at least one kind of solvent selected from the group consisting of alcohol and water is not particularly limited as long as it is not higher than the boiling point of the solvent and not lower than the temperature at which 2-amino-6-benzyloxypurine can be dissolved. When methanol (alone) is used as a solvent, it is generally 30° C.-65° C., preferably 55° C.-65° C.

In the event an insoluble material is present in a solution obtained by dissolving 2-amino-6-benzyloxypurine in a solvent containing at least one kind of solvent selected from the group consisting of alcohol and water, the insoluble material is preferably removed for improving purity. For example, the obtained solution is hot filtrated to remove an insoluble material. The hot filtration is conducted while maintaining the dissolution state of 2-amino-6-benzyloxypurine, and the temperature depends on the solvent to be used. When methanol (alone) is used as a solvent, the filtration is conducted generally at 30° C.-65° C., preferably at 50° C.-65° C.

The precipitation of a cubic crystal and a columnar crystal may be started by any means. For example, (1) 2-amino-6-benzyloxypurine is dissolved in a solvent containing at least one kind of solvent selected from the group consisting of alcohol and water, and the obtained solution is cooled, (2) 2-amino-6-benzyloxypurine is dissolved in a solvent containing at least one kind of solvent selected from the group consisting of alcohol and water, and the solvent is partially removed from the obtained solution, and the like.

Before precipitation of crystals by the above-mentioned method (1) or (2), a poor solvent may be added to supersaturate the solution.

When the precipitation of crystal is started by the method of the above-mentioned (1), the cooling temperature is set for Ti that affords a desired crystal shape, and 2-amino-6-benzyloxypurine in the solvent containing at least one kind of solvent selected from the group consisting of alcohol and water is cooled to reach supersaturation.

When the precipitation of crystal is started by the method of the above-mentioned (2), The evaporation temperature is set for Ti that affords a desired crystal shape, and the solvent is evaporated until 2-amino-6-benzyloxypurine in the solvent containing at least one kind of solvent selected from the group consisting of alcohol and water reaches supersaturation.

Once a crystal having the desired shape starts to precipitate, cooling or evaporation thereafter does not necessarily require setting the temperature for Ti. However, it is necessary to pay sufficient attention to prevent dissolution of the precipitated crystals. The precipitated crystals may be taken out by any means, such as filtration.

A cubic crystal is obtained as one without a solvent molecule, and a columnar crystal is obtained as a solvate (e.g., alcoholate, hydrate and the like), both by the above-mentioned method. For example, a columnar crystal can be converted to a crystal without a solvent molecule by drying at a temperature for removing the solvent molecule. The conversion to a crystal without a solvent molecule can be performed by drying the collected crystals at generally 60° C.-200° C., preferably 80° C.-120° C., in any solvent.

The production methods of an alcoholate and a hydrate of 2-amino-6-benzyloxypurine are explained in the following. The alcoholate should be obtained by crystallization from alcohol, and the hydrate should be obtained by crystallization from a water-containing solvent.

As the alcohol to obtain the alcoholate, a solvent similar to alcohol used for the production of the above-mentioned novel crystal can be used. The amount of the alcohol to be used for producing the alcoholate is not subject to any particular limitation as long as 2-amino-6-benzyloxypurine can be dissolved by heating, and varies depending on heating temperature. When methanol (alone) or ethanol (alone) is used, for example, the amount is generally 10 ml-1000 ml, preferably 10 ml-300 ml, relative to 1 g of 2-amino-6-benzyloxypurine when the heating temperature is in the following range.

As the solvent other than water that is contained in the water-containing solvent to be used for obtaining a hydrate, alcohol is preferably used. As the alcohol to be used here, a solvent similar to the above-mentioned alcohol used for the production of the novel crystal can be used. As the water-containing solvent, water alone and a mixed solvent of alcohol and water are preferably used. As the mixed solvent of alcohol and water, a mixed solvent of methanol and water is preferable in view of difference in solubility. The mixing ratio of alcohol and water depends on the kind of alcohol.

For example, in the case of a mixed solvent of methanol and water, the volume ratio of methanol and water is 10:3-10:50, preferably 10:8-10:15.

The temperature for dissolving 2-amino-6-benzyloxypurine in each solvent by heating is not particularly limited as long as 2-amino-6-benzyloxypurine can be dissolved in each solvent at said temperature. When methanol is used, the temperature is generally 30° C.-65° C., preferably 55° C.-65° C. The crystallization method after dissolution by heating is not particularly limited, and a method similar to crystallization in the production method of the above-mentioned novel crystal can be employed.

When the precipitation of crystal is conducted by the method of the aforementioned (1) or (2), crystallization at Ti for a columnar crystal affords a columnar crystal with a solvent molecule, and crystallization at Ti for a cubic crystal affords a cubic crystal without a solvent molecule. Thus, a cubic crystal with a solvent molecule cannot be obtained. The precipitated crystals may be taken out by any means, such as filtration.

When each crystal with a solvent molecule obtained is dried, it is necessary to pay sufficient attention to drying conditions to prevent removal of the solvent molecule. The drying temperature is generally 10° C.-70° C., preferably 10° C.-50° C., for any solvate.

Each step for producing the novel crystal and solvate of the present invention may be carried out under atmospheric pressure, under reduced pressure, or under pressurization.

The 2-amino-6-benzyloxypurine to be used in the present invention may be produced by any method. For example, it can be produced by the method described in JP-A-10-218880.

EXAMPLES

The present invention is explained in detail in the following by referring to Examples. The present invention is not limited by these examples.

The conditions for the measurement of each property of the compounds obtained in Examples and Reference Example are as follows.

DSC: measured using DSC-60 manufactured by Shimadzu Corporation.

$^1$H-NMR: A sample was dissolved in DMSO-$d_6$, which was measured by JNM-AL400 manufactured by JEOL Corporation.

microscopic photograph: photographed using SMZ1500 manufactured by Nikon.

powder X-ray diffraction: measured using Mini Flex manufactured by Rigaku Corporation.

Reference Example 1

Benzyl alcohol (37.5 g, 0.347 mol) and sodium hydroxide (2.96 g, 0.074 mol) were mixed and heated, and sodium hydroxide was dissolved. After cooling, 2-amino-6-chloropurine (6.00 g, 0.035 mol) was added, and the reaction was completed by heating and stirring at 80-90° C. for 5 hr. Methyl tert-butyl ether (120 ml) was added to the reaction mixture, and the mixture was extracted twice with 1% aqueous sodium hydroxide solution (70 ml). The obtained aqueous alkali layers were combined, washed with toluene, and after removing toluene, neutralized with 35% hydrochloric acid to pH 6-8. The precipitated crystals were collected by filtration. The obtained crystals were dried under reduced pressure to give 2-amino-6-benzyloxypurine (7.60 g, 0.032 mol, yield 92%) as crude crystals.

Example 1

Figure 2:
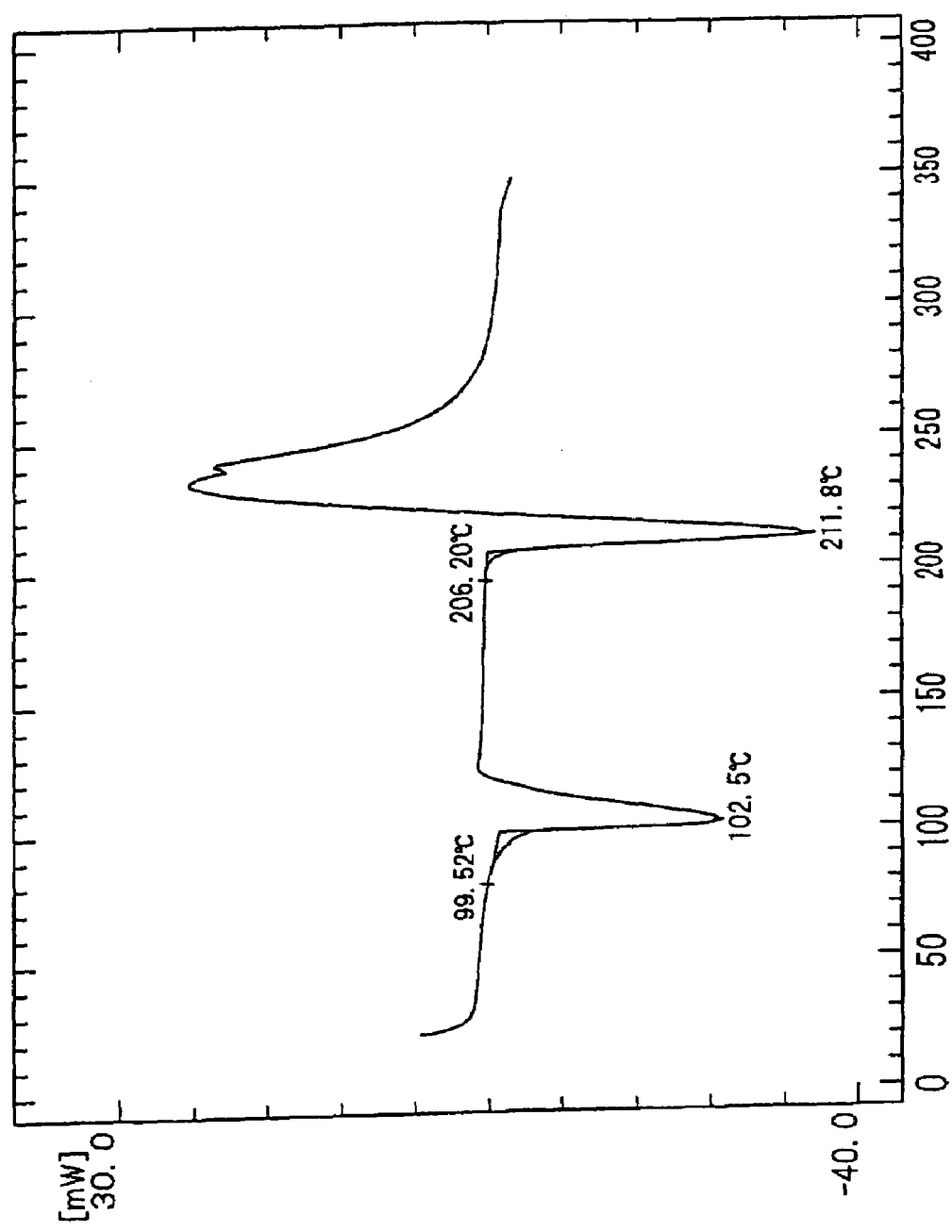
FIG. 2 shows a differential scanning calorimetry (DSC) of a 2-amino-6-benzyloxypurine hydrate, which is a columnar crystal obtained in Example 1.

2-Amino-6-benzyloxypurine (40.0 g, 0.17 mol) obtained in Reference Example 1 was dissolved in methanol (700 ml) by heating under reflux (63° C.-65° C.). This solution was hot filtered (60° C.-63° C.), and then methanol (350 ml) was evaporated under reduced pressure at 40° C.-45° C., as a result of which crystals started to precipitate. Water (400 ml) was added thereto, and the mixture was cooled to 0° C.-5° C. to allow further precipitation of crystals. After filtration, the crystals were dried under reduced pressure at room temperature for 12 hr to give a 2-amino-6-benzyloxypurine hydrate (41.7 g, 0.16 mol, yield 97%) as columnar crystals. The reduction in amount by drying (110° C., 4 hr) was 7.52%. The microscopic photograph of the obtained compound is shown in FIG. 1, and DSC thereof is shown in FIG. 2.

Example 2

Figure 3:
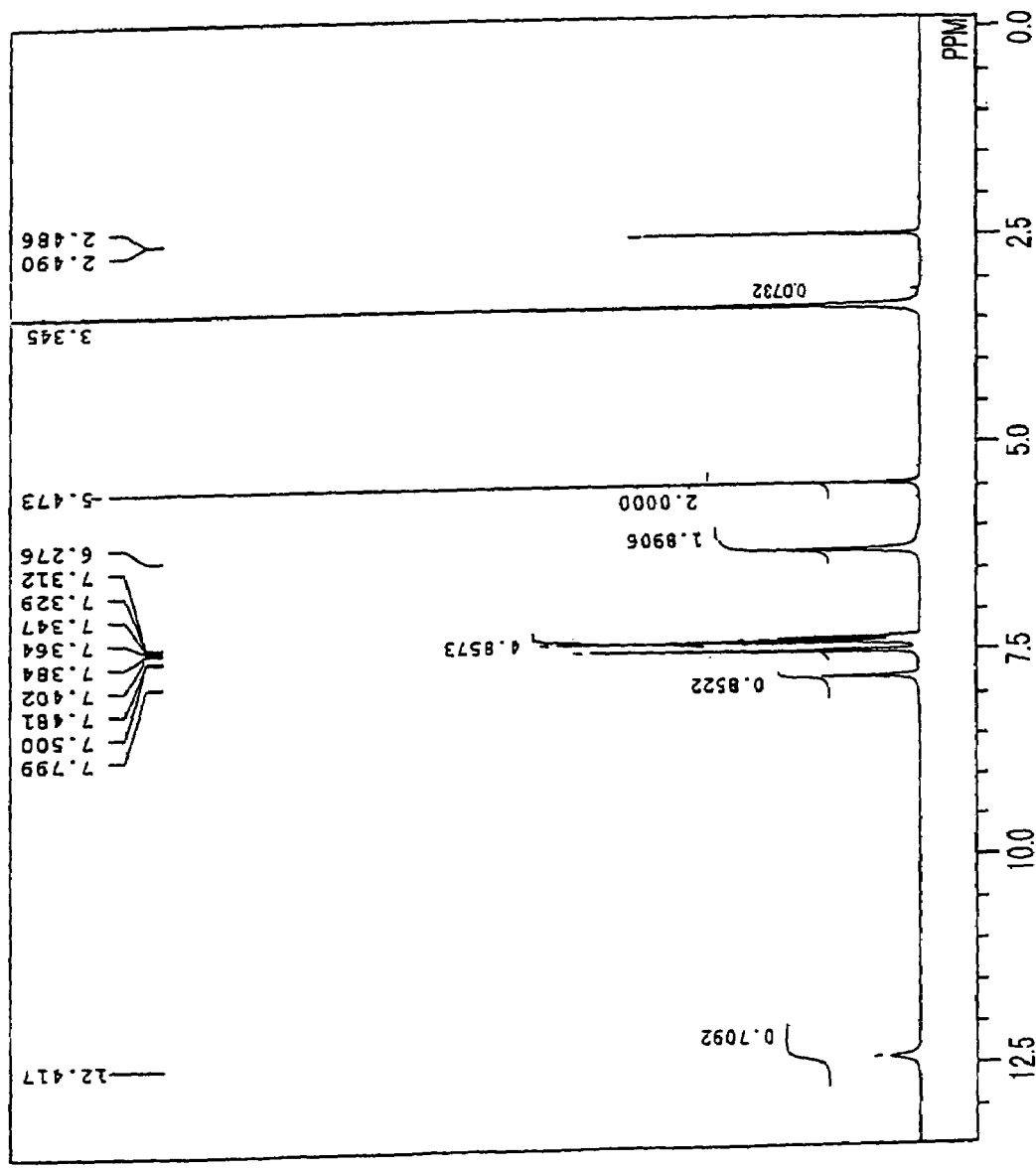
FIG. 3 shows $^1$H-NMR of 2-amino-6-benzyloxypurine, which is a cubic crystal obtained in Example 2.
Figure 4:
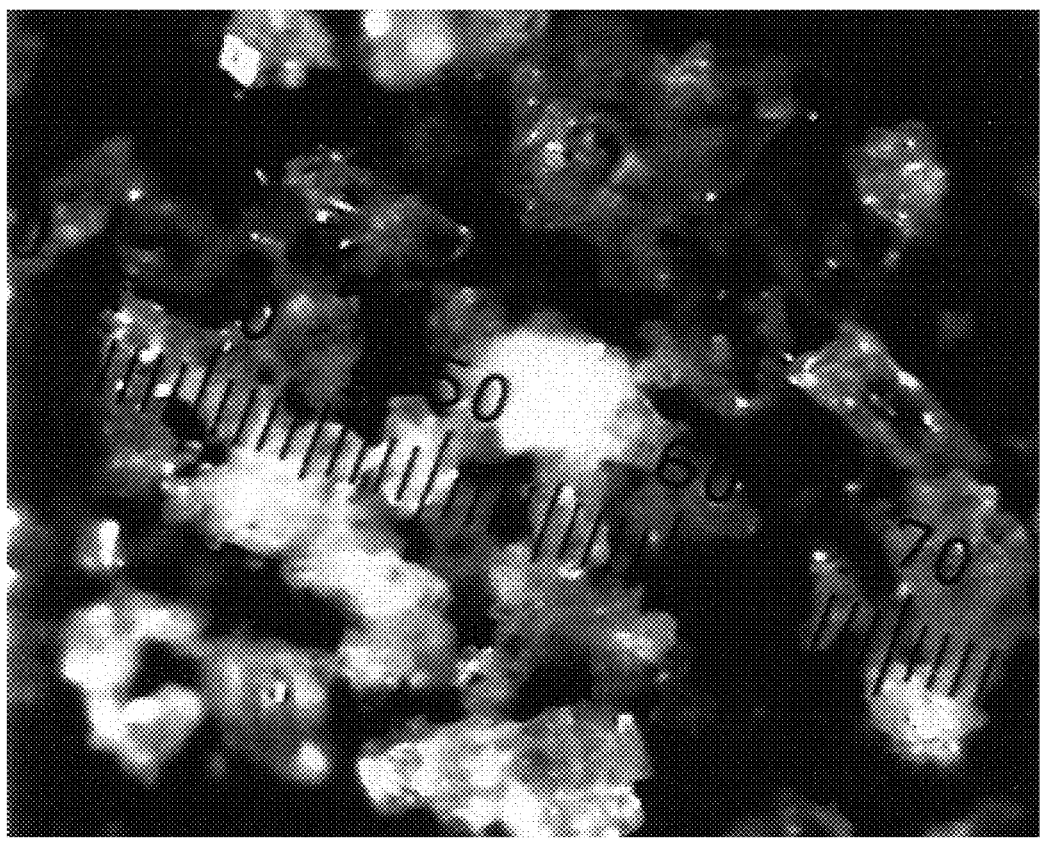
FIG. 4 shows a microscopic photograph (magnification× 100, 1 graduation=0.02 mm) of 2-amino-6-benzyloxypurine, which is a cubic crystal obtained in Example 2.
Figure 5:
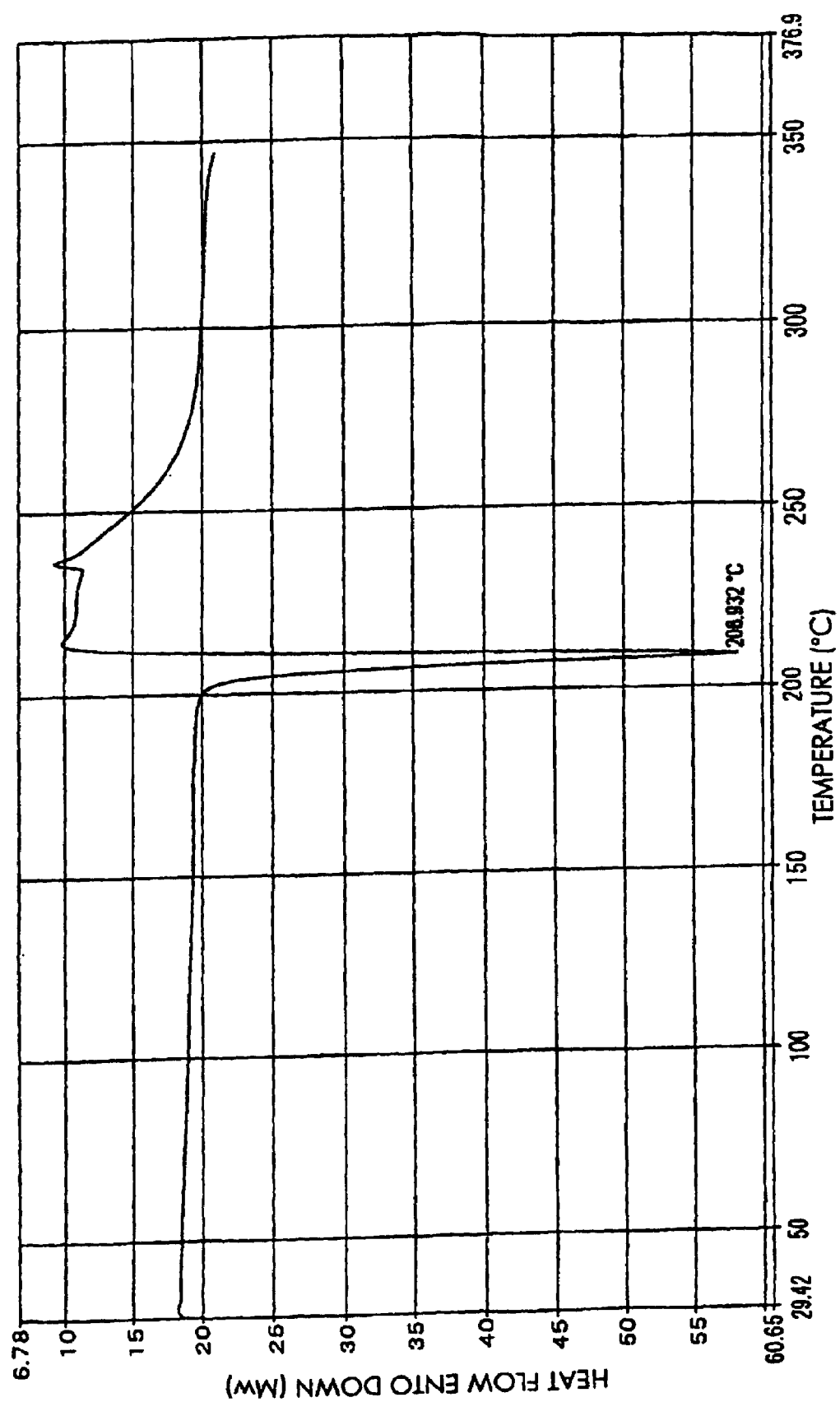
FIG. 5 shows DSC of 2-amino-6-benzyloxypurine, which is a cubic crystal obtained in Example 2.
Figure 6:
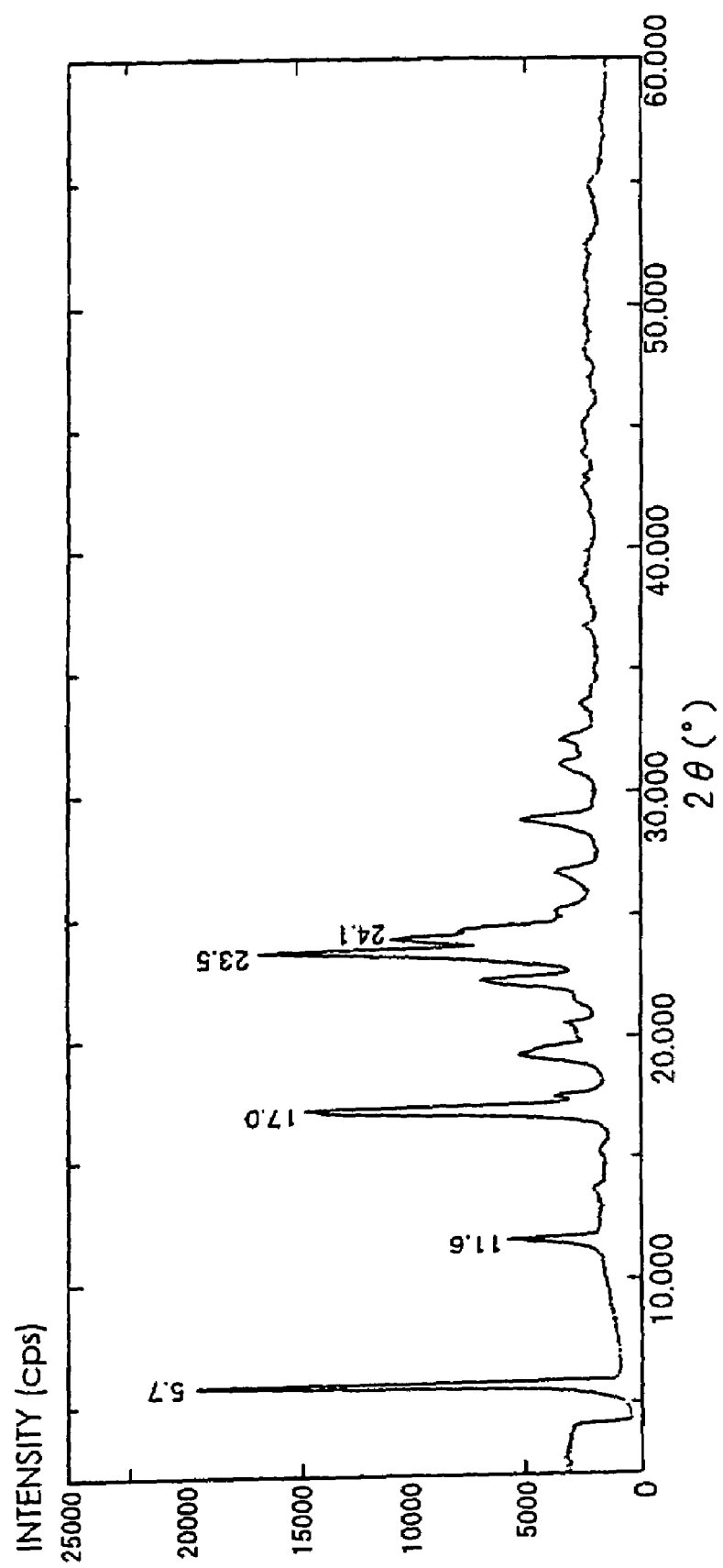
FIG. 6 shows powder X-ray diffraction of 2-amino-6-benzyloxypurine, which is a cubic crystal obtained in Example 2.

2-Amino-6-benzyloxypurine (20.0 g, 0.083 mol) obtained in Reference Example 1 was dissolved in methanol (300 ml) by heating under reflux. This solution was hot filtered (60° C.-63° C.), and methanol (150 ml) was evaporated under atmospheric pressure at 63° C.-65° C., as a result of which crystals started to precipitate. This was cooled to 0° C.-5° C. over 30 min. After filtration, the crystals were dried under reduced pressure at 50° C. for 6 hr to give a 2-amino-6-benzyloxypurine hydrate (17.9 g, 0.074 mol, yield 89%) as cubic crystals. The reduction in amount by drying (110° C., 4 hr) was 0.02%. The $^1$H-NMR of the obtained compound is shown in FIG. 3, microscopic photograph thereof is shown in FIG. 4, DSC thereof is shown in FIG. 5 and powder X-ray diffraction thereof is shown in FIG. 6.

Example 3

Figure 7:
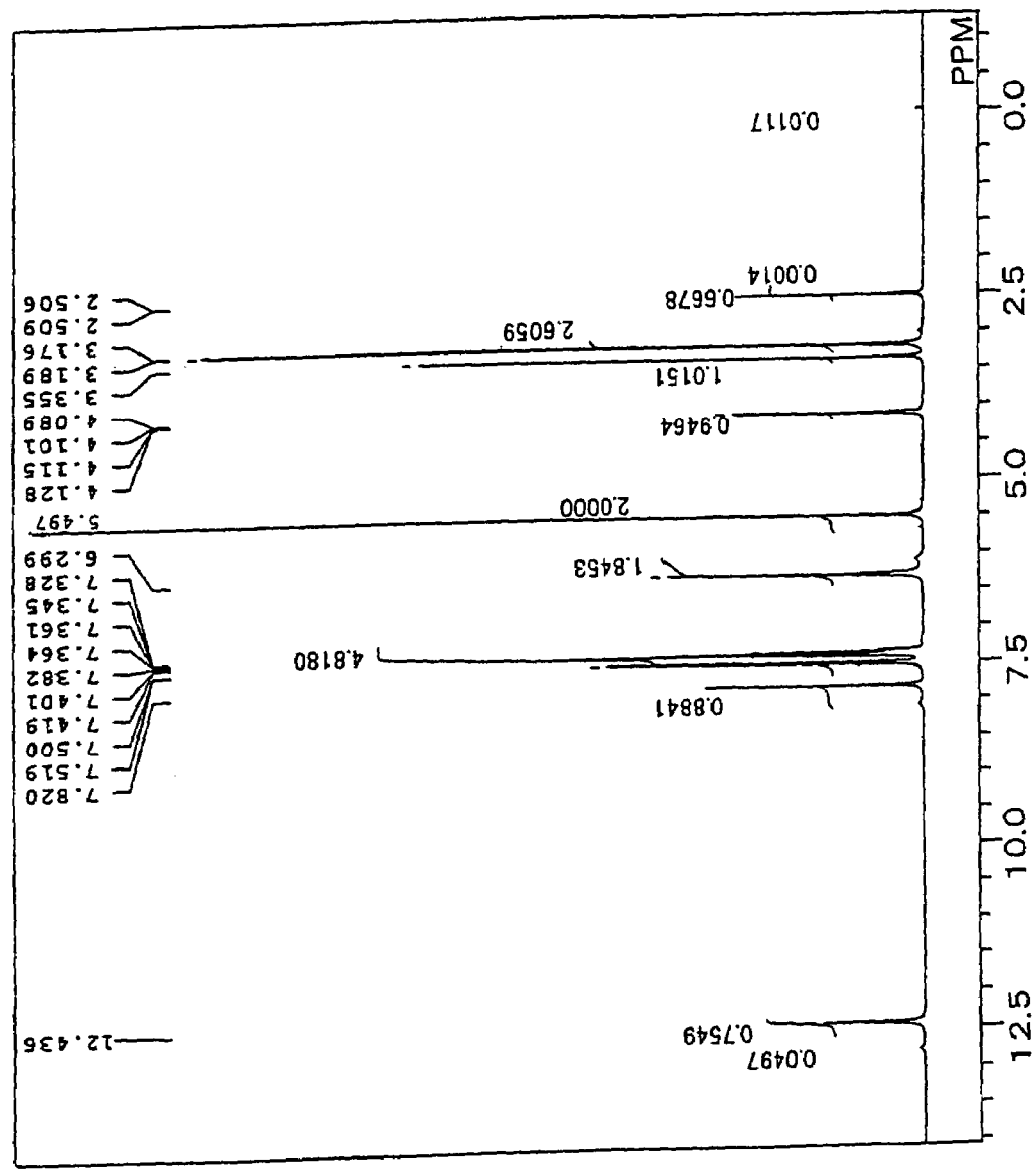
FIG. 7 shows $^1$H-NMR of a 2-amino-6-benzyloxypurine methanolate, which is a columnar crystal obtained in Example 3.
Figure 8:
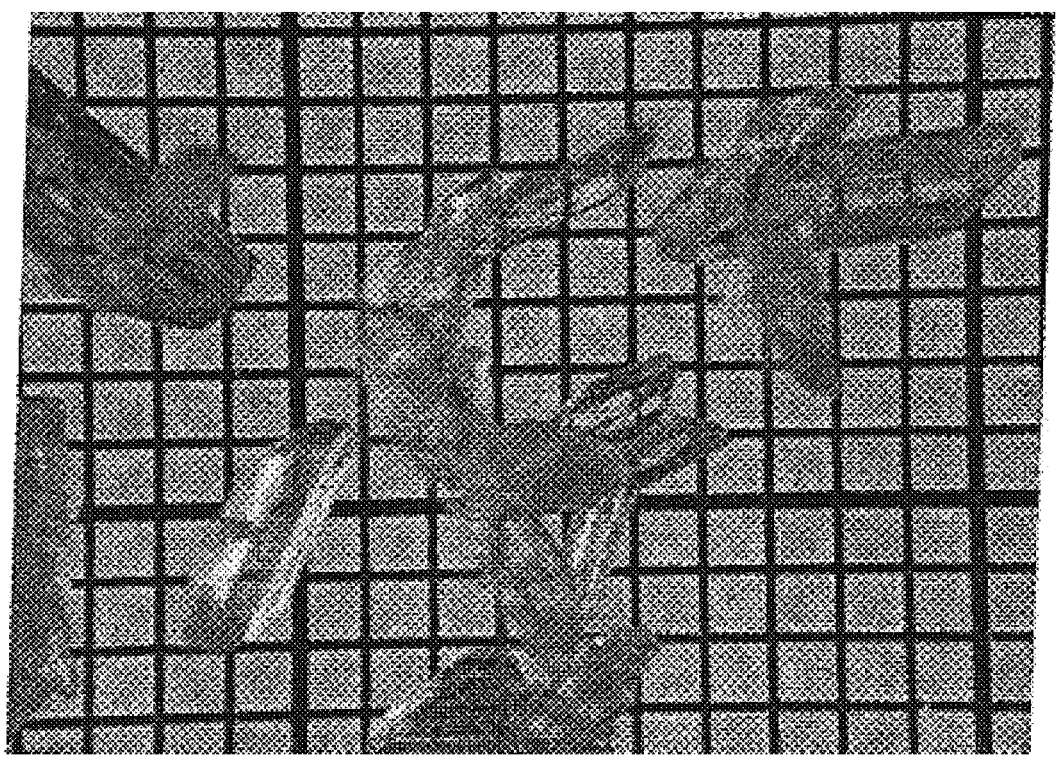
FIG. 8 shows a microscopic photograph (1 cell=0.1 mm) of a 2-amino-6-benzyloxypurine methanolate, which is a columnar crystal obtained in Example 3.
Figure 9:
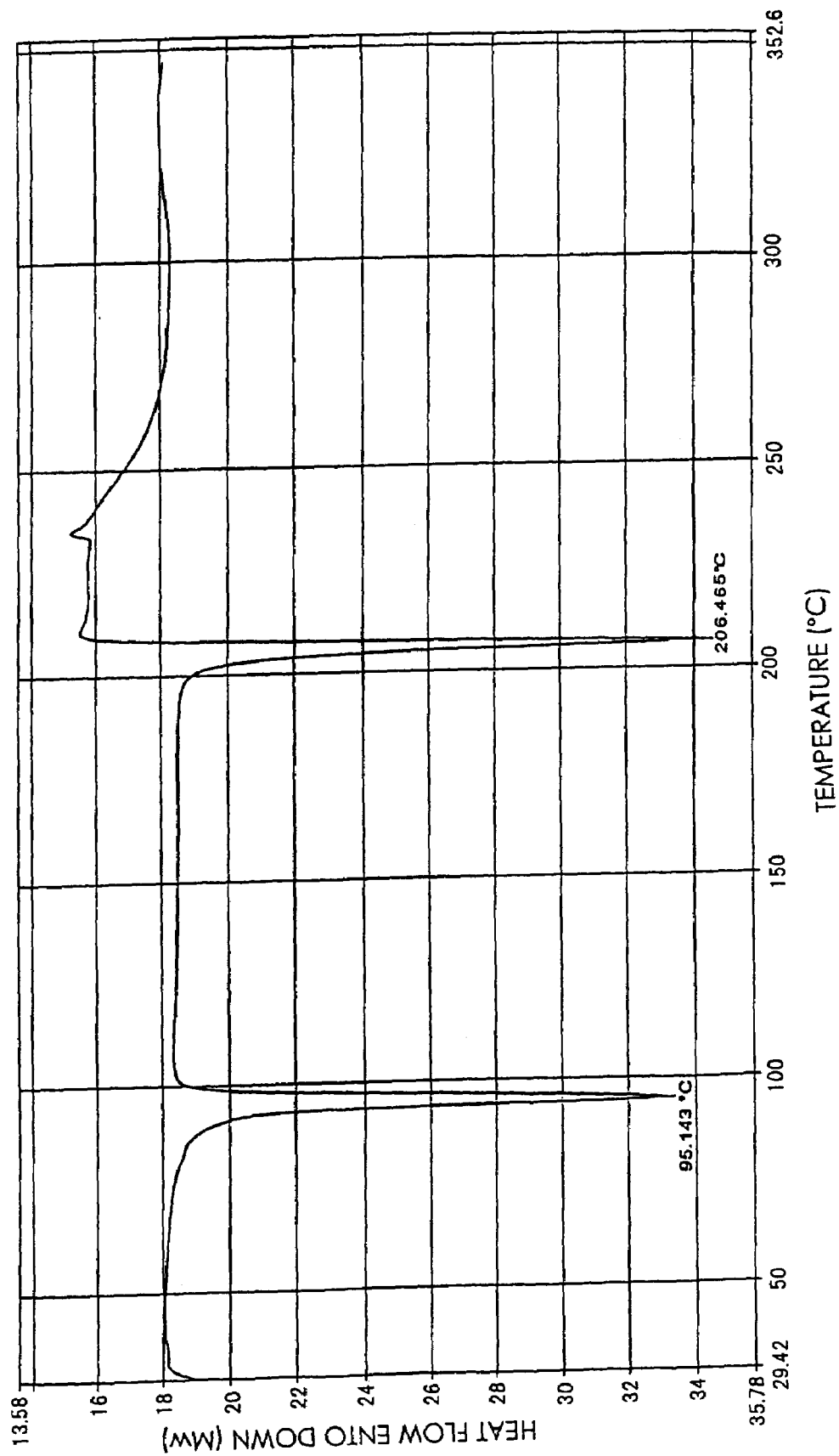
FIG. 9 shows DSC of a 2-amino-6-benzyloxypurine methanolate, which is a columnar crystal obtained in Example 3.
Figure 10:
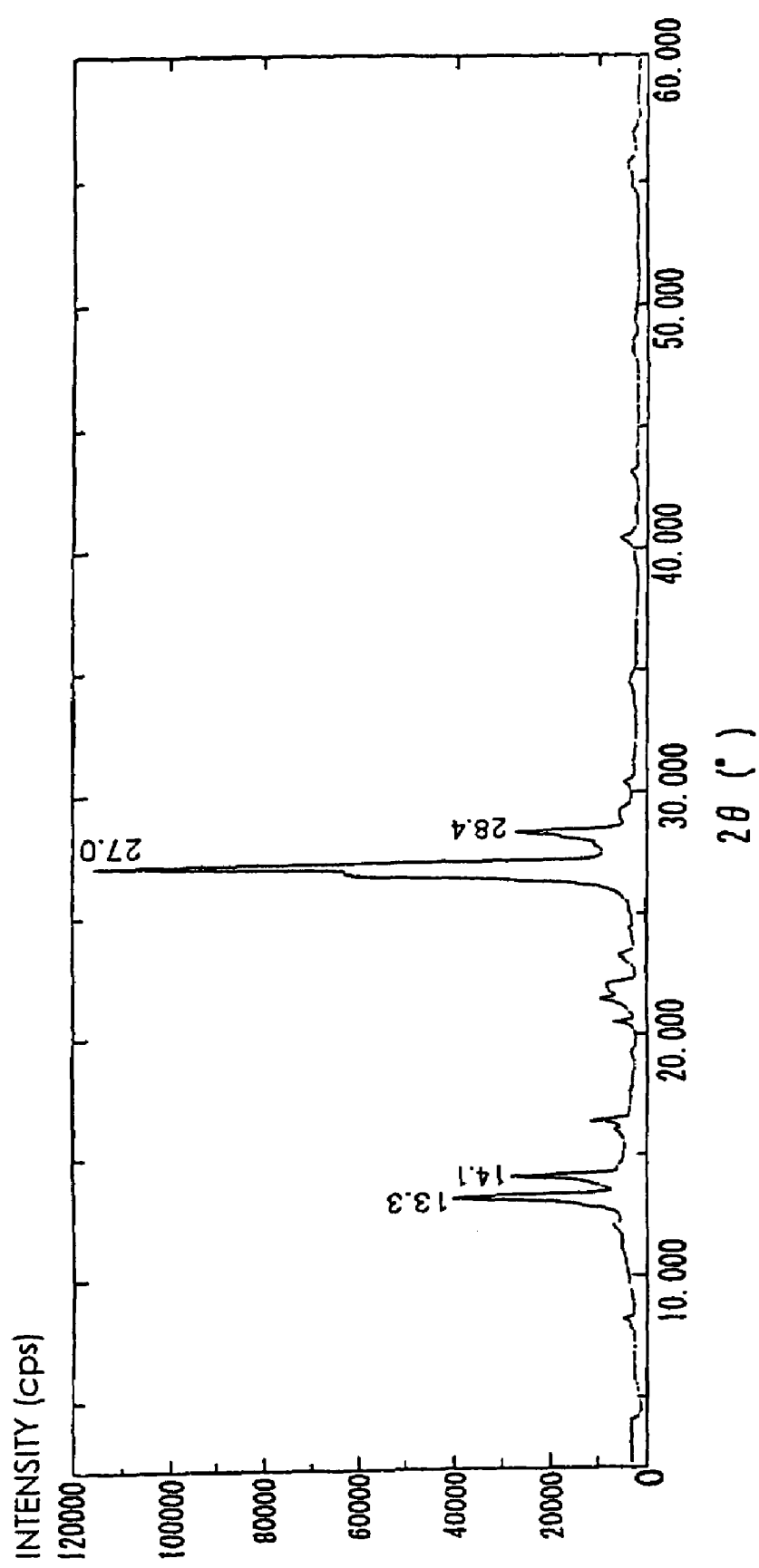
FIG. 10 shows powder X-ray diffraction of a 2-amino-6-benzyloxypurine methanolate, which is a columnar crystal obtained in Example 3.

2-Amino-6-benzyloxypurine (20 g, 0.083 mol) obtained in Reference Example 1 was dissolved in methanol (300 ml) by heating under reflux. This solution was hot filtered (60° C.-63° C.), and methanol (150 ml) was evaporated under reduced pressure at 40° C.-45° C., as a result of which crystals started to precipitate. This was cooled to 0° C.-5° C. over 6 hr. After filtration, the crystals were dried under reduced pressure at 45° C. for 6 hr to give a 2-amino-6-benzyloxypurine methanolate (21.5 g, 0.079 mol, yield 95%) as columnar crystals. The reduction in amount by drying (110° C., 4 hr) was 13.4%. The $^1$H-NMR of the obtained compound is shown in FIG. 7, microscopic photograph thereof is shown in FIG. 8, DSC thereof is shown in FIG. 9 and powder X-ray diffraction thereof is shown in FIG. 10.

Example 4

Figure 11:
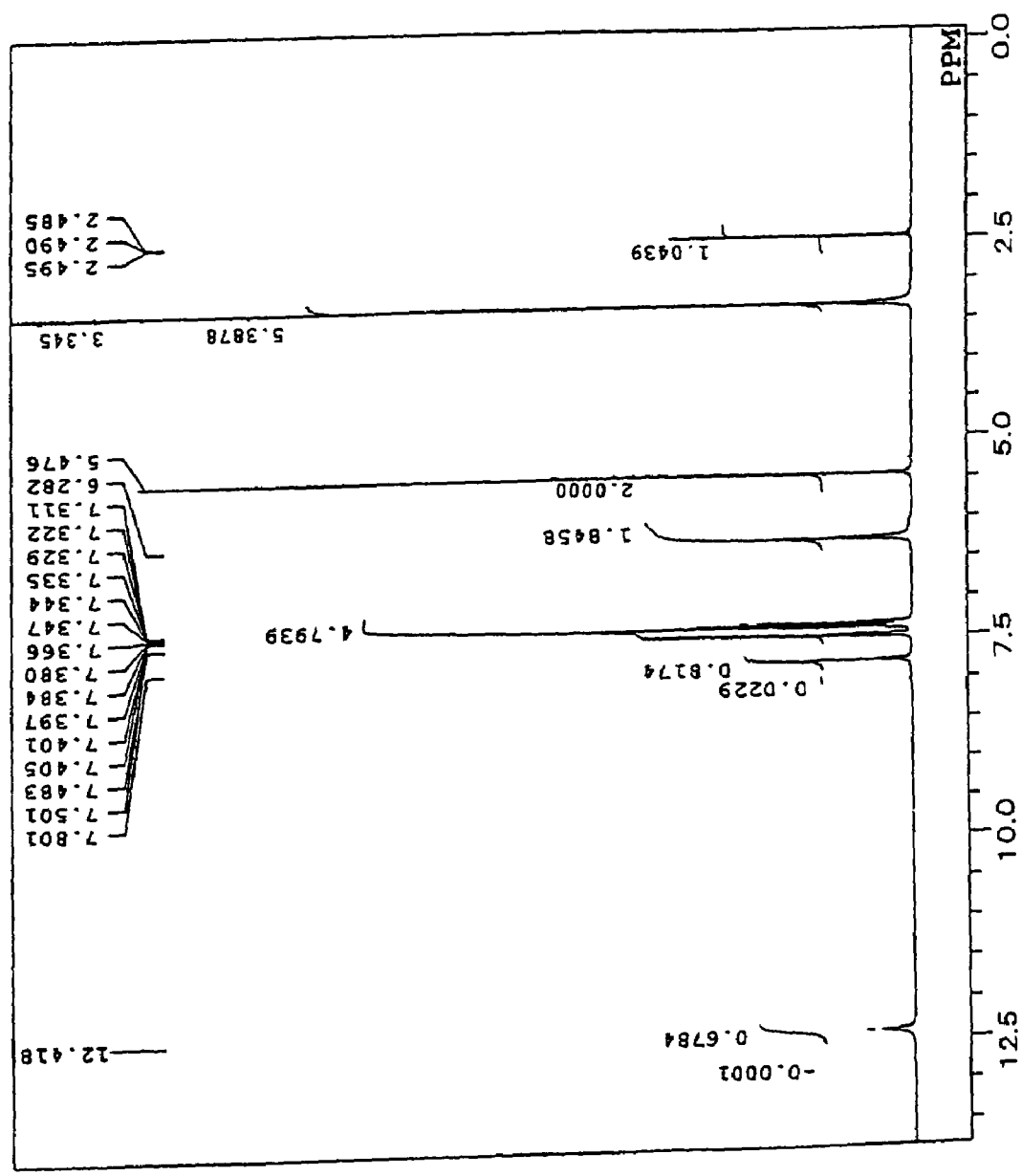
FIG. 11 shows $^1$H-NMR of 2-amino-6-benzyloxypurine without a solvent molecule, which is a columnar crystal obtained in Example 4.
Figure 12:
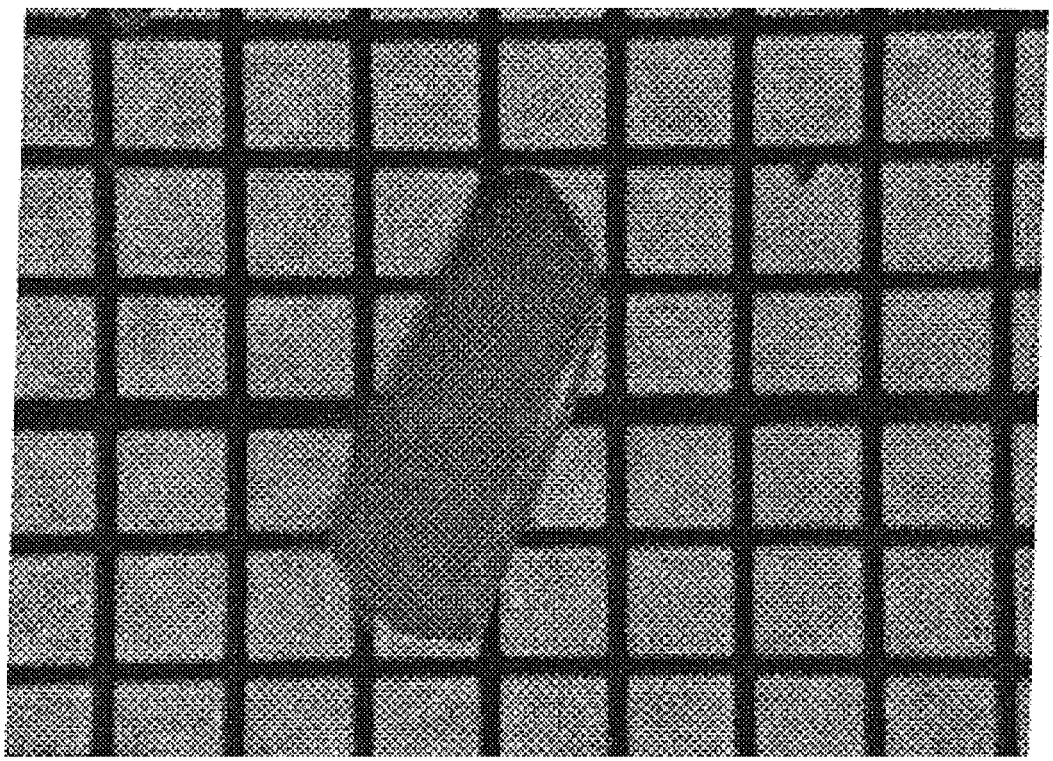
FIG. 12 shows a microscopic photograph (1 cell=0.1 mm) of 2-amino-6-benzyloxypurine without a solvent molecule, which is a columnar crystal obtained in Example 4.
Figure 13:
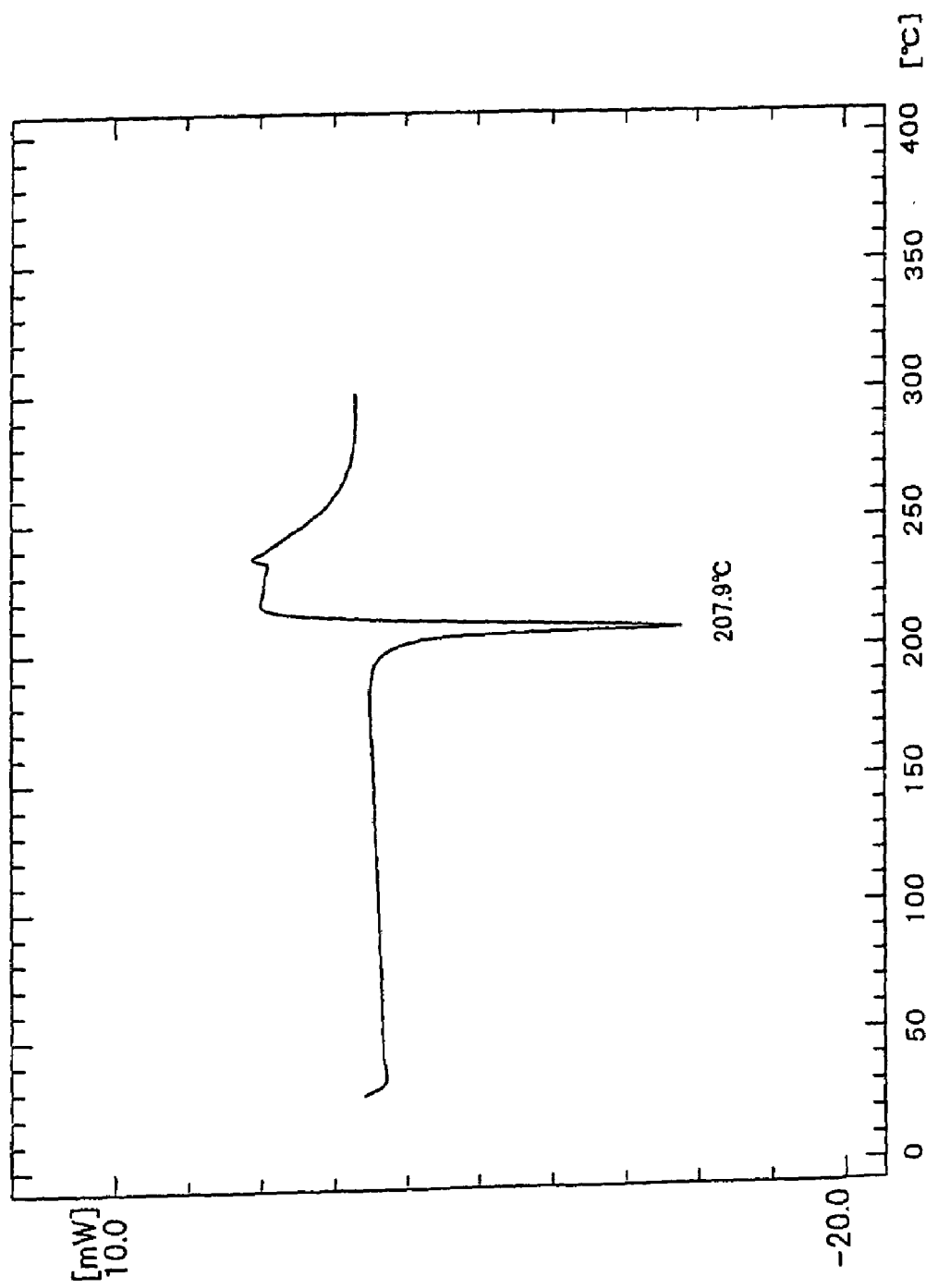
FIG. 13 shows DSC of 2-amino-6-benzyloxypurine without a solvent molecule, which is a columnar crystal obtained in Example 4.
Figure 14:
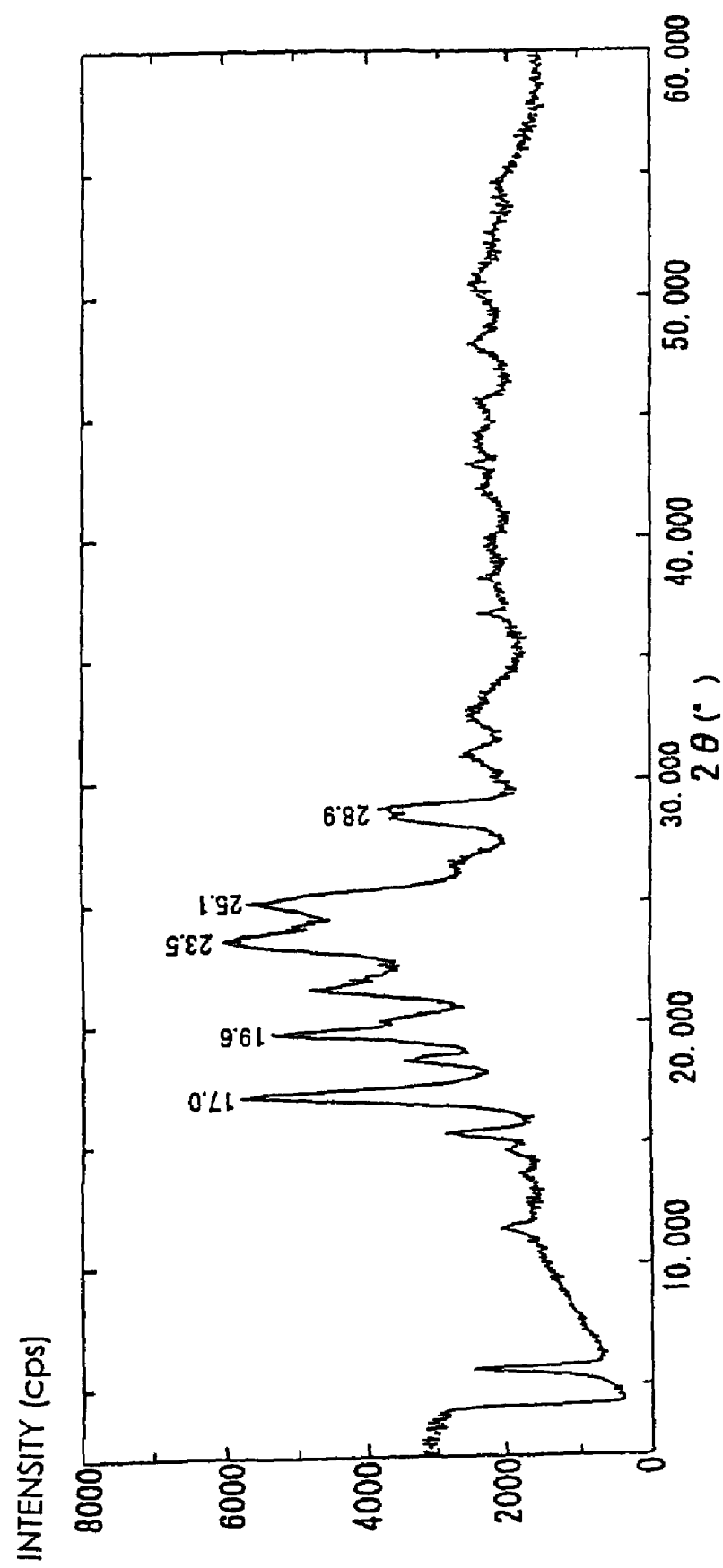
FIG. 14 shows powder X-ray diffraction of 2-amino-6-benzyloxypurine without a solvent molecule, which is a columnar crystal obtained in Example 4.

By drying the crystal (10 g, 0.036 mol) obtained in Example 3 under reduced pressure (15 mmHg) at 90° C. for 7 hr, 2-amino-6-benzyloxypurine without a solvent molecule (8.8 g, 0.036 mol) was obtained as columnar crystals. The $^1$H-NMR of the obtained compound is shown in FIG. 11, microscopic photograph thereof is shown in FIG. 12, DSC thereof is shown in FIG. 13 and powder X-ray diffraction thereof is shown in FIG. 14.

Example 5

Figure 15:
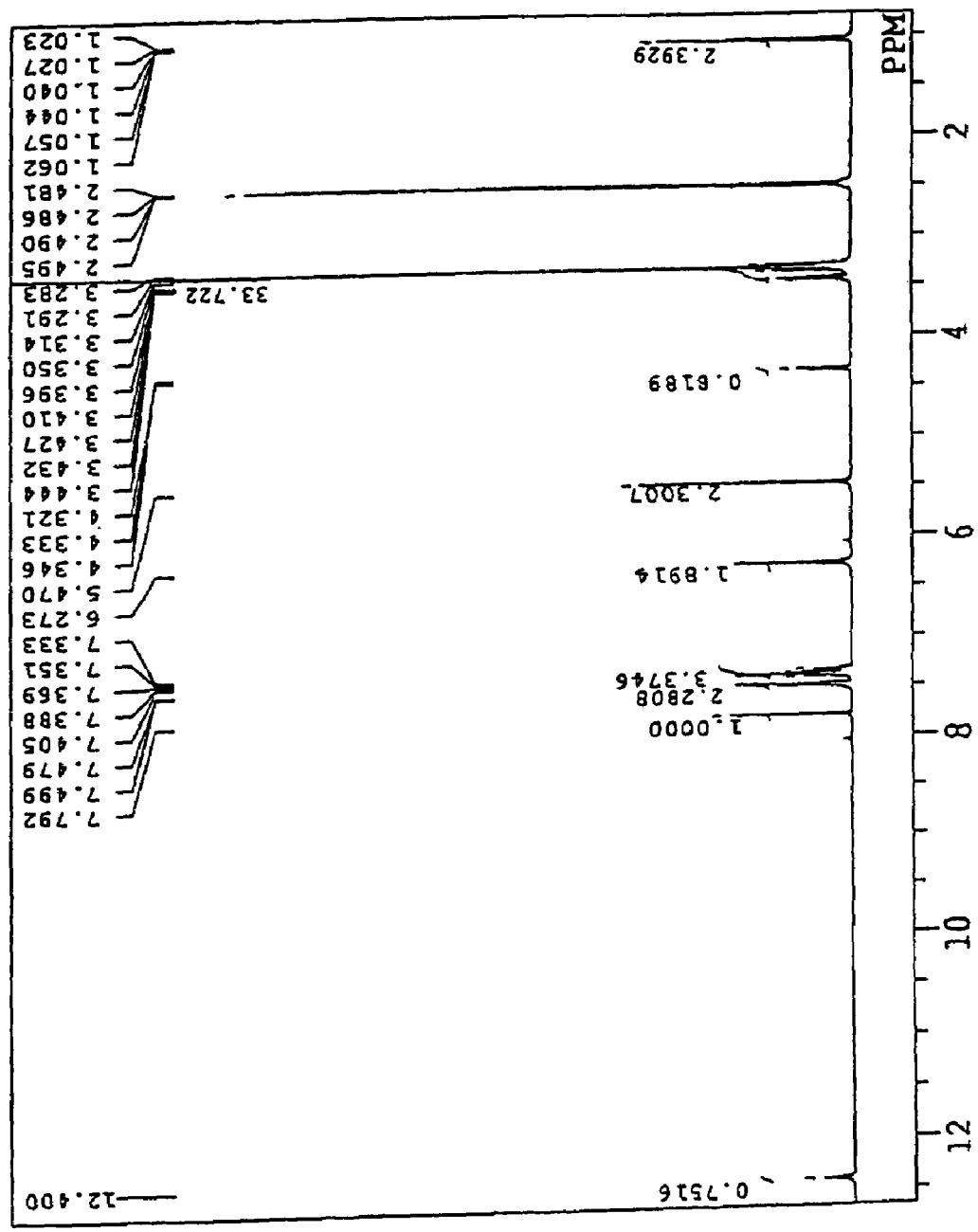
FIG. 15 shows $^1$H-NMR of a 2-amino-6-benzyloxypurine ethanolate, which is a columnar crystal obtained in Example 5.
Figure 16:
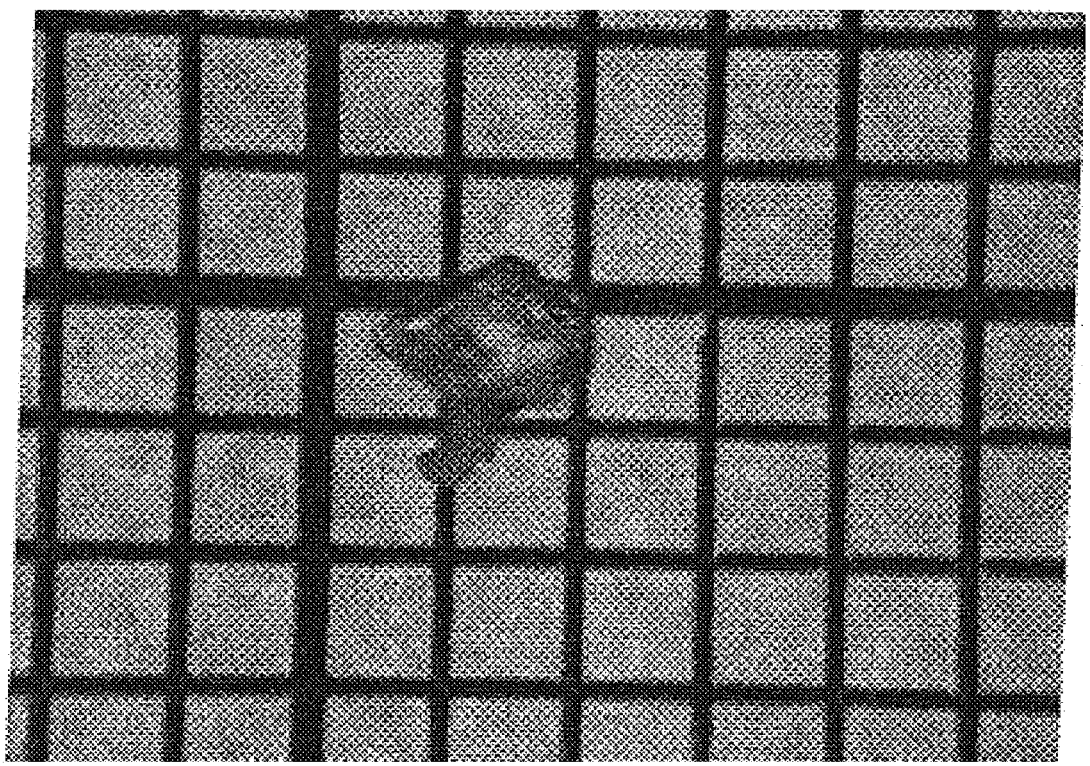
FIG. 16 shows a microscopic photograph (1 cell=0.1 mm) of a 2-amino-6-benzyloxypurine ethanolate, which is a columnar crystal obtained in Example 5.
Figure 17:
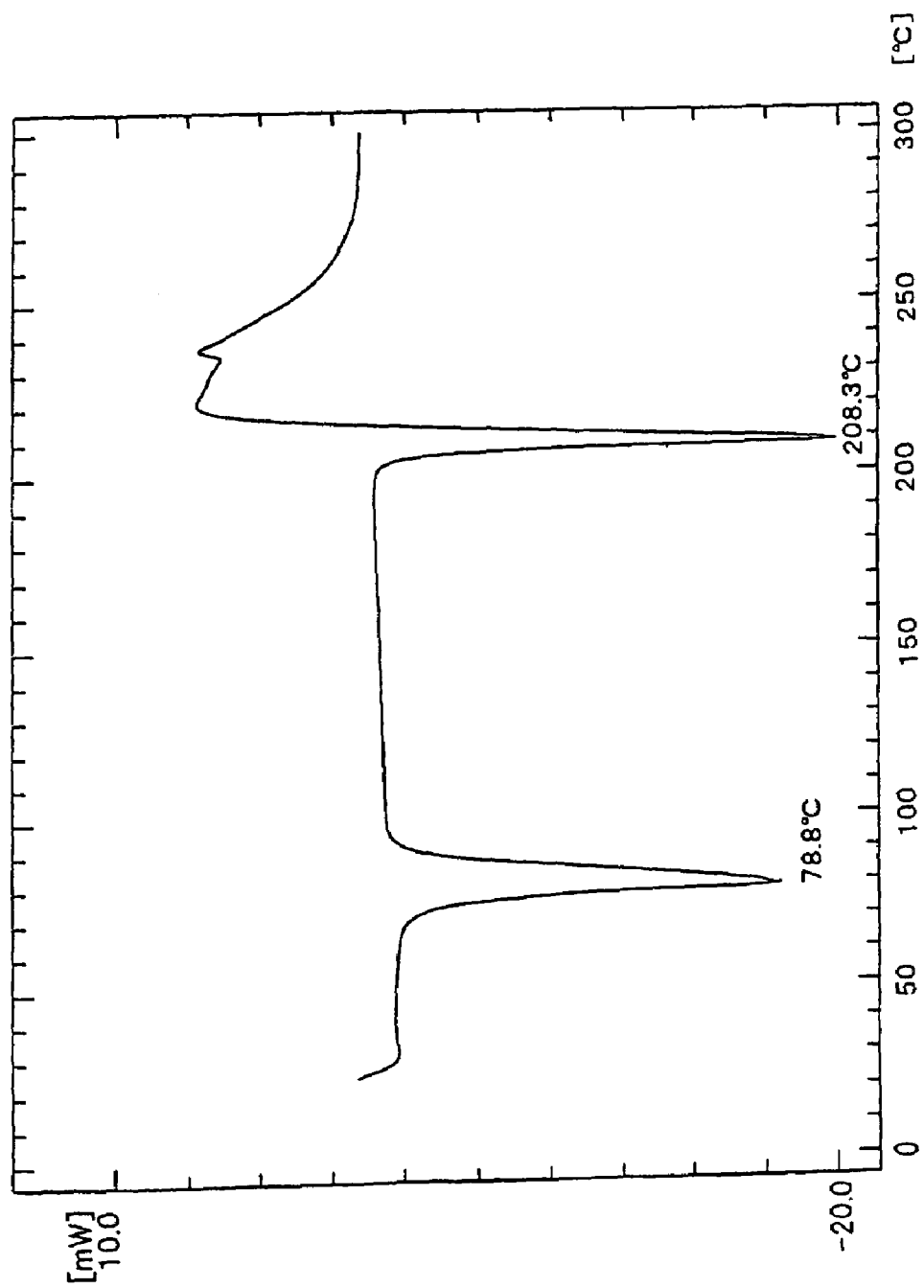
FIG. 17 shows DSC of a 2-amino-6-benzyloxypurine ethanolate, which is a columnar crystal obtained in Example 5.
Figure 18:
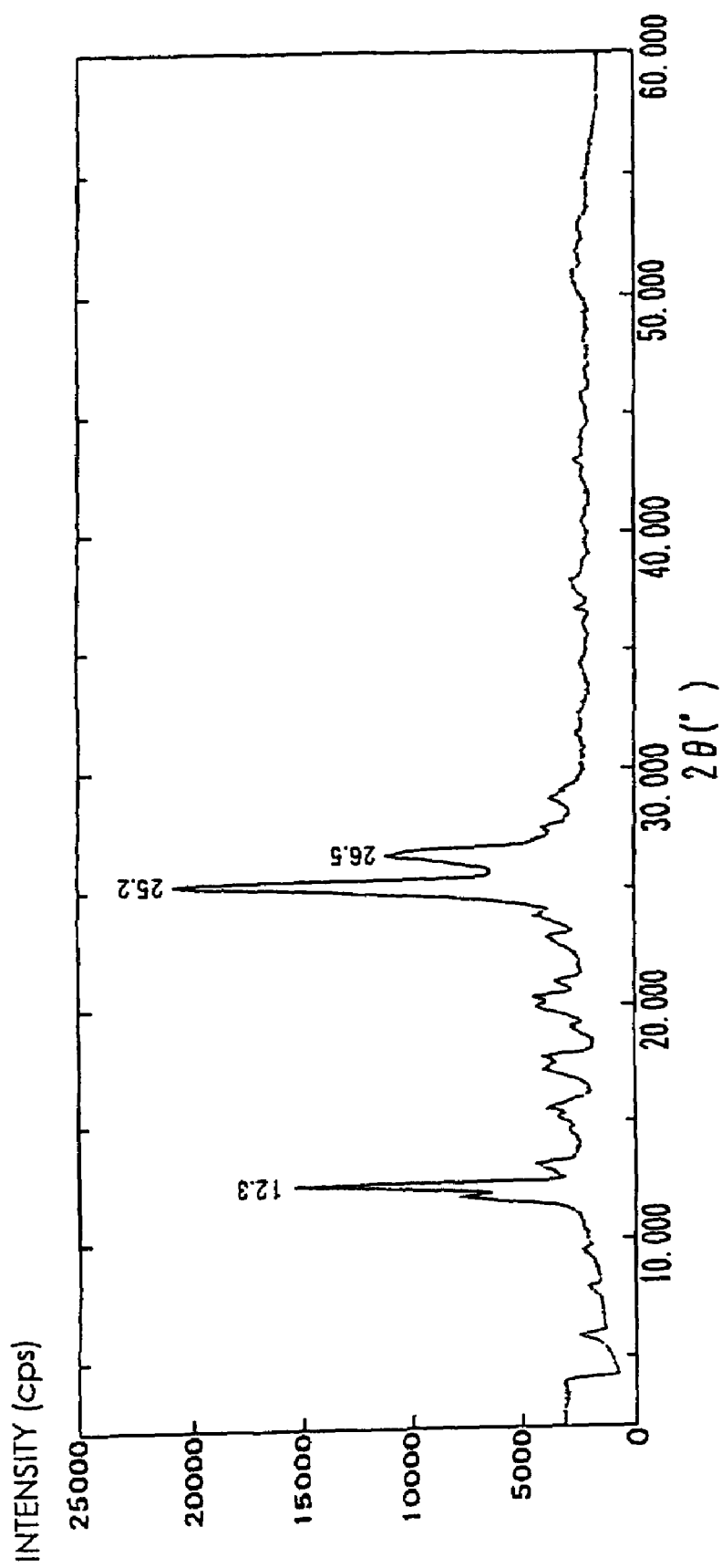
FIG. 18 shows powder X-ray diffraction of a 2-amino-6-benzyloxypurine ethanolate, which is a columnar crystal obtained in Example 5.

By treating 2-amino-6-benzyloxypurine (20 g, 0.0083 mol) obtained in Reference Example 1 in the same manner as in Example 3 except that ethanol (300 ml) was used instead of methanol, a 2-amino-6-benzyloxypurine ethanolate (22.1 g, 0.078 mol, yield 93%) was obtained as columnar crystals. The crystal started to precipitate when the solution was cooled. The temperature then was about 45° C. The reduction in amount by drying (110° C., 4 hr) was 16.4%. The $^1$H-NMR of the obtained compound is shown in FIG. 15, microscopic photograph thereof is shown in FIG. 16, DSC thereof is shown in FIG. 17 and powder X-ray diffraction thereof is shown in FIG. 18.

INDUSTRIAL APPLICABILITY

According to the present invention, a novel crystal (cubic crystal or columnar crystal) and a solvate (hydrate and alcoholate (e.g., methanolate, ethanolate) of 2-amino-6-benzyloxypurine, which have not been obtained before, and production methods thereof can be provided.

The crystal obtained by the method of the present invention is superior in filtering performance and has improved operability as compared to conventional crystals.

This application is based on a patent application No. 2002-105805 filed in Japan, the contents of which are hereby incorporated by reference.

The invention claimed is:

1. A 2-amino-6-benzyloxypurine methanolate.
2. A columnar crystal of 2-amino-6-benzyloxypurine methanolate.
3. A production method of a 2-amino-6-benzyloxypurine methanolate, which comprises crystallizing 2-amino-6-benzyloxypurine from methanol.

* * * * *